US011937982B2

(12) United States Patent
Savord et al.

(10) Patent No.: US 11,937,982 B2
(45) Date of Patent: Mar. 26, 2024

(54) 2D ARRAY ULTRASOUND PROBE WITH 3 WATT DIGITAL MICROBEAMFORMER

(71) Applicant: KONINKLIJKE PHILIPS N.V., Eindhoven (NL)

(72) Inventors: Bernard Joseph Savord, Andover, MA (US); Antonia Cornelia Van Rens, Nuenen (NL); Sotir Filipov Ouzounov, Eindhoven (NL); McKee Dunn Poland, Andover, MA (US); Nik Ledoux, Merrimack, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 61 days.

(21) Appl. No.: 17/713,423

(22) Filed: Apr. 5, 2022

(65) Prior Publication Data

US 2022/0225962 A1 Jul. 21, 2022

Related U.S. Application Data

(63) Continuation of application No. 15/681,546, filed on Aug. 21, 2017, now Pat. No. 11,317,893.

(60) Provisional application No. 62/382,849, filed on Sep. 2, 2016.

(51) Int. Cl.
*A61B 8/00* (2006.01)
*G01S 7/52* (2006.01)
*G01S 15/89* (2006.01)
*G10K 11/34* (2006.01)

(52) U.S. Cl.
CPC .............. *A61B 8/4494* (2013.01); *A61B 8/56* (2013.01); *G01S 7/52023* (2013.01); *G01S 7/5208* (2013.01); *G01S 7/52085* (2013.01); *G01S 7/52095* (2013.01); *G01S 7/52096* (2013.01); *G01S 15/8925* (2013.01); *G10K 11/341* (2013.01); *G10K 11/346* (2013.01); *A61B 8/4461* (2013.01)

(58) Field of Classification Search
CPC ....... A61B 8/4461; A61B 8/4494; A61B 8/56; G01S 15/8925; G01S 7/52023; G01S 7/5208; G01S 7/52085; G01S 7/52095; G01S 7/52096; G10K 11/341; G10K 11/346
See application file for complete search history.

(56) References Cited

U.S. PATENT DOCUMENTS

| | | |
|---|---|---|
| 5,229,933 A | 7/1993 | Larson, III |
| 5,997,479 A | 12/1999 | Savord et al. |
| 6,013,032 A | 1/2000 | Savord |
| 6,126,602 A | 10/2000 | Savord et al. |
| 6,375,617 B1 | 4/2002 | Fraser |
| 7,037,264 B2 | 5/2006 | Poland |
| 7,821,180 B2 | 10/2010 | Kunkel |
| 7,927,280 B2 | 4/2011 | Davidsen |
| 2014/0058270 A1 | 2/2014 | Davidsen et al. |
| 2015/0099978 A1 | 4/2015 | Davidsen et al. |

*Primary Examiner* — Mark D Remaly

(57) ABSTRACT

An ultrasound probe has a two dimensional matrix array transducer and a digital microbeamformer. The microbeamformer comprises a plurality of transmitters and amplifiers coupled to elements of the array transducer, a plurality of low power analog to digital converters and digital beamforming circuitry coupled to the amplifiers, a microbeamformer controller, a power supply and a USB controller which cumulatively consume three watts or less.

19 Claims, 9 Drawing Sheets

2D ARRAY ULTRASOUND PROBE WITH 3 WATT DIGITAL MICROBEAMFORMER

CROSS-REFERENCED APPLICATIONS

This application is a continuation application of U.S. patent application Ser. No. 15/681,546, filed on Aug. 21, 2017, which in turn claims the benefit of U.S. Provisional Patent Application No. 62/382,849, filed on Sep. 2, 2016. This application is hereby incorporated by reference herein.

This invention relates to medical diagnostic ultrasound systems and, in particular, to two dimensional array ultrasound probes with digital microbeamformers consuming 3 watts or less.

Ultrasonic array transducers use beamformers to transmit and appropriately delay and sum the ultrasonic echo signals received from elements of the transducer array. The delays are chosen in consideration of the direction (steering) and focus depth of the beams to be formed by the beamformer. After the signals received from each element have been properly delayed by a channel of the beamformer, the delayed signals are combined to form a beam of properly steered and focused coherent echo signals. During ultrasonic beam transmission, the time of actuation of individual elements is the complement of the receive delay, steering and focusing the transmit beam. The choice of delays is known to be determinable from the geometry of the array elements and of the image field being interrogated by the beams.

In a traditional ultrasound system the array transducer is located in a probe which is placed against the body of the patient during imaging and contains some electronic components such as tuning elements, switches, and amplification devices. The delaying and signal combining is performed by the beamformer which is contained in the ultrasound system mainframe, to which the probe is connected by a cable.

The foregoing system architecture for an array transducer and a beamformer suffices quite well for most one dimensional (1D) transducer arrays, where the number of transducer elements and the number of beamformer channels are approximately the same. When the number of transducer elements exceeds the number of beamformer channels, multiplexing is generally employed and only a subset of the total number of elements of the transducer can be connected to the beamformer at any point in time. The number of elements in a 1D array can range from less than one hundred to several hundred and the typical beamformer has 128 beamformer channels. This system architecture solution became untenable with the advent of two dimensional (2D) array transducers for two and three dimensional (3D) imaging. That is because 2D array transducers steer and focus beams in both azimuth and elevation over a volumetric region. The number of transducer elements needed for this beam formation is usually in the thousands. The crux of the problem then becomes the cable that connects the probe to the system mainframe where the beamformer is located. A cable of several thousand conductors of even the finest conductive filaments becomes thick and unwieldy, making manipulation of the probe cumbersome if not impossible.

A solution to this problem is to perform at least some of the beamforming in the probe itself, as described in U.S. Pat. No. 5,229,933 (Larson, III). In the ultrasound system shown in this patent, the beamforming is partitioned between the probe and the system mainframe. Initial beamforming of groups of elements is done in the probe by microcircuitry known as a microbeamformer, where partially beamformed sums are produced. These partially beamformed sums, being fewer in number than the number of transducer elements, are coupled to the system mainframe through a cable of reasonable dimensions, where the beamforming process is completed and the final beam produced. The partial beamforming in the probe is done by what Larson, III refers to as intragroup processors, in a microbeamformer in the form of microelectronics attached to the array transducer. See also U.S. Pat. No. 5,997,479 (Savord et al.); U.S. Pat. No. 6,013,032 (Savord); U.S. Pat. No. 6,126,602 (Savord et al.); and U.S. Pat. No. 6,375,617 (Fraser). The thousands of connections between the thousands of elements of the transducer array and the microbeamformer are done at the tiny dimensions of the microcircuitry and the array pitch, while the many fewer cable connections between the microbeamformer and the beamformer of the system mainframe are done by more conventional cable technologies. Various planar and curved array formats can be used with microbeamformers such as the curved arrays shown in U.S. Pat. No. 7,821,180 (Kunkel, III) and U.S. Pat. No. 7,927,280 (Davidsen). Microbeamformers can also be used with one dimensional arrays and with 2D arrays operated as one dimensional arrays. See, e.g., U.S. Pat. No. 7,037,264 (Poland).

For many years now beamforming in an ultrasound system has been done digitally. The received signals are delayed by clocked shift registers or the time of temporary storage in a random access memory and the delayed signals are summed by digital adders. The digital beamforming can be performed in circuitry such as an FPGA (field programmable gate array) or by software instructions in a microprocessor. But to perform the beamforming digitally the received signals must first be digitized by analog to digital converters. In today's commercially available ultrasound probes with microbeamformers, the partial sum signals are formed in the microbeamformer by operating on the received echo signals in their native analog domain. The analog partial sum signals are coupled to the system mainframe over the probe cable, where they are digitized and beamformation is completed in the digital domain. Recently, the beamforming technology has been integrated even further in the L12-4 linear and the C5-2 curved array probes of Philips Healthcare's Lumify™ ultrasound products. Digitization and digital beamforming is performed by microcircuitry located in the handle of the probe, as is signal detection and image formation by scan conversion. These probes, however, use 1D (one dimensional) array transducers with far fewer transducer elements than those of a 2D array probe for 3D imaging. It would be desirable for the entire beamformation circuitry to be located in the probe for both 1D array (two dimensional imaging) and 2D array (three dimensional imaging) probes.

A problem which must be surmounted when integrating all of the beamforming circuitry in the probe is due to the power consumption by the microcircuitry. This problem is heat dissipation from the circuitry. Since the probe is held by the hand of an ultrasonographer during scanning, all of the heat generated by the internal circuitry of the probe will cause the probe to feel warm to the touch. At times, the probe handle can feel uncomfortably hot to the touch, a problem which must be prevented. Passive probe cooling arrangements have been devised, as well as active systems which convey heat away from the probe where it dissipated away from the user, such as those described in US Pat. pub. no. 2014/0058270 (Davidsen et al.) and US Pat. pub. no. 2015/0099978 (Davidsen et al.) However, such arrangements significantly increase the cost and complexity of the probe and its cable. It would be desirable to avoid such arrangements by the far simpler expedient of reduced power consumption by the microcircuitry.

In accordance with the principles of the present invention, microbeamformer circuitry is described which performs digital beamforming in an ultrasound probe for a two dimensional (2D) matrix array transducer. Elements of the array are actuated by transmitters located on an IC, which are coupled to array elements. Power consumption is reduced by using a low power digital-to-analog conversion technique such as delta-sigma or successive approximation analog to digital conversion. Preferably, the ADCs are located on a common IC with the digital beamforming circuitry. This enables the microbeamformer chip set to operate within a power budget of 3 watts or less, thereby avoiding excessive heat generation within the probe.

Figure 1:
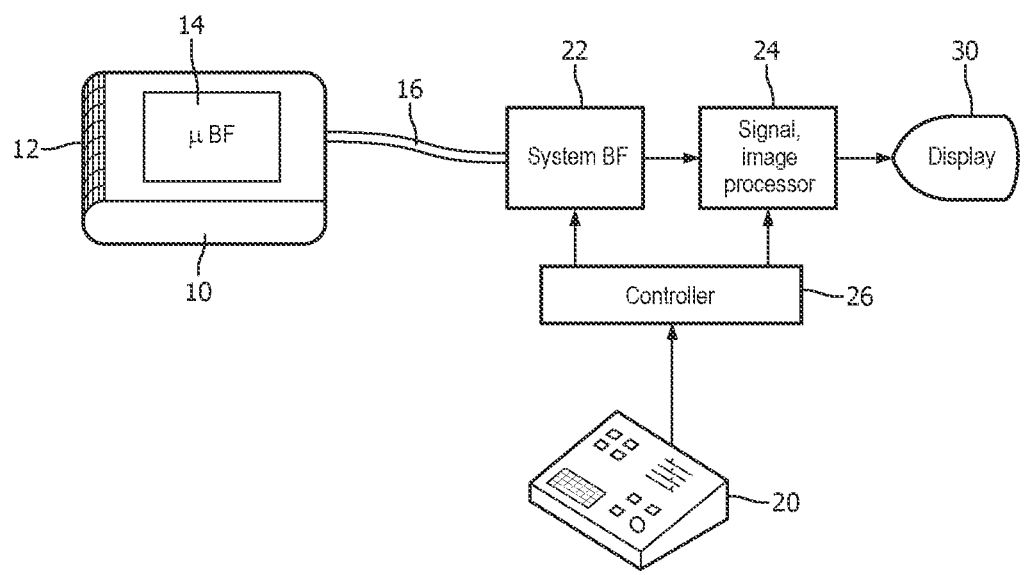
FIG. 1 illustrates in block diagram form an ultrasonic imaging system constructed in accordance with the principles of the present invention.

Referring first to FIG. 1, an ultrasound system constructed in accordance with the principles of the present invention is shown in block diagram form. A probe 10 has a two dimensional array transducer 12 which may be planar or curved as shown in this example. The transducer may be formed of MUT devices such as CMUTs (capacitive micromachined ultrasonic transducers) or PVDF, but is preferably formed of a piezoceramic material such as PZT. The elements of the array are coupled to a digital microbeamformer 14 located in the probe behind the transducer array. A microbeamformer is integrated circuitry located in the probe with beamforming channels coupled to elements of the 2D array transducer 12. The microbeamformer applies timed transmit pulses to elements of each group of elements (patch) of the array to transmit beams in the desired directions and to the desired focal points in the image field in front of the array. The profile of the transmit beams in the elevation dimension can exhibit a point focus, a plane wave, or any intermediate beam profile. Echoes returned by cells and tissue from the transmitted beams are received by the array elements and coupled to channels of the microbeamformer 14 where the analog echo signals are individually delayed. The delayed signals from a contiguous patch of transducer elements are combined to form a partial sum signal for the patch. In the analog section of the microbeamformer described more fully below, combining is done by coupling the delayed signals from the elements of the patch to a common bus, obviating the need for summing circuits. The analog echo signals are then digitized and further beamformed in digital form by a digital ASIC (application specific integrated circuit). The beamformed digital signals of each patch are coupled to a system beamformer 22 in an ultrasound system by way of a cable 16, where the beamforming process is completed. Alternatively, in a preferred implementation all of the beamforming is performed by the microbeamformer in the probe, and fully beamformed digital signals coupled to the system mainframe. The beamformed digital signals are used to form an image by a signal and image processor 24, which may perform operations such as baseband detection, harmonic separation, filtering, Doppler processing, and scan conversion for image formation. The signal and image processor 24 produces 2D or 3D images for display on an image display 30. The signal and image processor may comprise electronic hardware components, hardware controlled by software, or a microprocessor executing image processing algorithms. It generally will also include specialized hardware or software which processes received echo data into image data for images of a desired display format such as a scan converter.

Control of ultrasound system parameters such as probe selection, beam steering and focusing, and signal and image processing is done under control of a system controller 26 which is coupled to various modules of the system and to the microbeamformer in the probe 10 as described more fully below. The system controller may be formed by ASIC circuits or microprocessor circuitry and software data storage devices such as RAMs, ROMs, or disk drives. In the case of the probe 10 some of this control information is provided to the microbeamformer from the system mainframe over data lines of the cable 16, conditioning the microbeamformer for operation of the transducer array as required for the particular scanning procedure. The user controls these operating parameters by means of a control panel 20.

Figure 2:
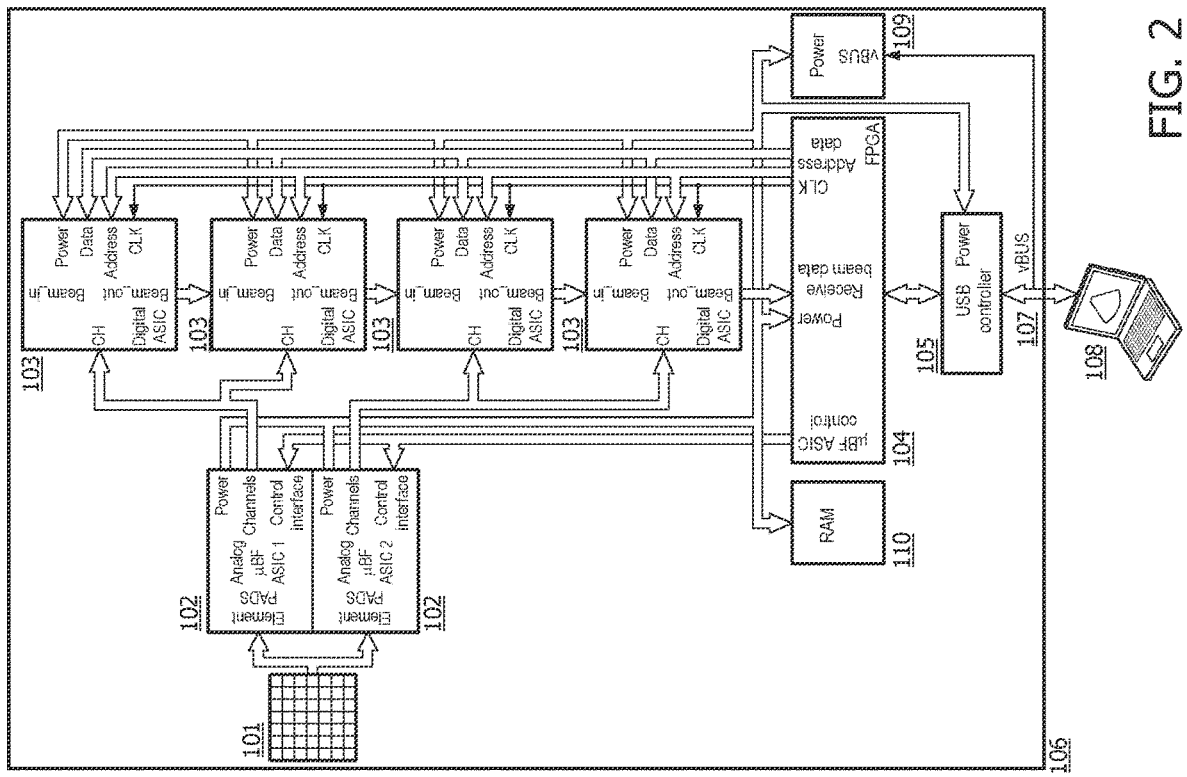
FIG. 2 illustrates in block diagram form the microbeamforming circuits and transducer array of an ultrasound probe of the present invention coupled to a portable computer as the display device.

FIG. 2 illustrates a digital microbeamformer in an ultrasound probe 106 which operates a 2D (two dimensional) matrix array transducer 101 having 8192 transducer elements operated in 128 groups of sixty-four elements configured as 8×8 patches. The microbeamformer in the illustrated implementation comprises two analog ASICS 102, each coupled to half of the elements of the matrix array 101. The analog ASICs contain transmit circuitry, transmit/receive (T/R) switches, preamplifying amplifiers and analog delays as described more fully below. The analog ASICs 102 are coupled to four digital ASICs 103 of the microbeamformer that contain low power analog to digital converters and digital beamforming circuitry. An FPGA 104 receives control data from the user operating a control and display device, show here as a laptop computer 108. The control and display device can alternatively be a cart-borne ultrasound system, a tablet computer, a PDA, a smartphone, or similar digital device with a display and user interface. The FPGA is coupled to the microbeamformer ASICs to provide control information for ultrasonic transmission and receive beam formation, and also stores data in a RAM (random access memory) 110 and manages a USB controller 105 and a switching power supply 109. The RAM 110 stores all of the control data necessary for each anticipated scanning mode of the probe. For example, the RAM 110 may be coupled to a write address controller to write digital echo signals into the RAM, and to a plurality of read address controllers, each adapted to controlling the reading of delayed digital echo signals for a different digital multiline echo signal. All of these circuits must operate in accordance with a chosen power budget, which is 3.0 watts in this example, in order to maintain a cool handheld probe. An exemplary power budget for the microbeamformer circuits shown in FIG. 2 is illustrated in Table 1 below.

TABLE 1

Power draw of FIG. 2 circuits for conditions indicated

| Component | Operation | Power |
|---|---|---|
| Transmit function of Analog ASIC | Transmit with 4096 elements | 0.75 W |
| Preamplifier and Delay circuits of Analog ASIC | Receive with 8192 elements, beamform to 128 partial sum signals | 0.5 W |
| USB 3.0 controller | 3Gb/s data transfer | 0.7 W |
| Control FPGA | Data management | 0.25 W |
| Power supply | Assumes 90% efficiency | 0.3 W |
| Digital ASIC | 128 ADCs sampling at 20 Mhz and digital beam formation with 8x multiline outputs | 0.5 W |
| Total | | 3.0 W |

This power budget shows that the entire microbeamformer circuitry, its control FPGA, power supply, and USB controller operate within a power allocation of 3.0 watts, thereby generating very little heat in the probe. The analog ASICs 102 produce 128 partial sum analog signals from 128 patches of sixty-four elements each, which are the 128 input signals for 128 ADCs in the digital ASICs. The microbeamformer may thus be viewed as a 128-channel digital beamformer. Dividing the power allocation by the number of channels shows that the microbeamformer consumes only about 23 milliwatts per channel. And each digital channel in the preferred implementation produces eight multilines for high frame rate digital imaging, which is a power consumption of only about 3 milliwatts per multiline scanline.

Thus, the ultrasound probe of the present invention provides a plurality of digital channels, wherein the power consumption per single multiline scanline can be as low as 3 milliwatts. In another embodiment, in which each digital channel produces four multilines, the power consumption is below or about 6 milliwatts per multiline scanline.

In the illustrated implementation of FIG. 2, the acoustic elements of the matrix array transducer 101 are connected directly to element pads of the analog ASICs 102 in a flip chip type interconnect. Control and group output signals are connected between the analog ASICs and the other components of the microbeamformer through a flexible interconnect (e.g., flex circuit) to a printed circuit board containing the other probe circuitry. Other interconnect techniques such as stacked silicon dies, ceramic circuits or multi-chip modules may also be employed. Each analog ASIC has sixty-four channel line outputs (CHANNELS) which conduct partially beamformed analog signals of sixty-four patches of elements to the channel inputs (CH) of two of the digital ASICs. Each digital ASIC thus processes thirty-two channels of partial sum signals. The FPGA 104 supplies control data to the analog ASICs from its μBF ASIC CONTROL bus to the CONTROL INTERFACE inputs of the analog ASICs 102. The FPGA supplies digital address data and control data to the digital ASICs 103 over ADDRESS and DATA buses, respectively, as well as a clock (CLK) signal. Digital beamformed output signals are propagated and summed from one digital ASIC to the next using BEAM IN and BEAM OUT buses connected from ASIC to ASIC until the fully summed digital echo signal is applied from the last ASIC to the RECEIVE BEAM DATA input of the FPGA.

The FPGA applies the fully beamformed output signals to the USB controller 105, which then transmits the digital echo signals as serial data over a USB cable 107 to the user control and display system 108. Other high speed digital interfaces such as HDMI or Ethernet can also be used. A suitable USB controller is the FX3.0s controller available from Cypress Semiconductor of San Jose, California. The switched power supply 109 is shown applying necessary power to the POWER inputs of all of the ICs of the microbeamformer.

Figure 3:
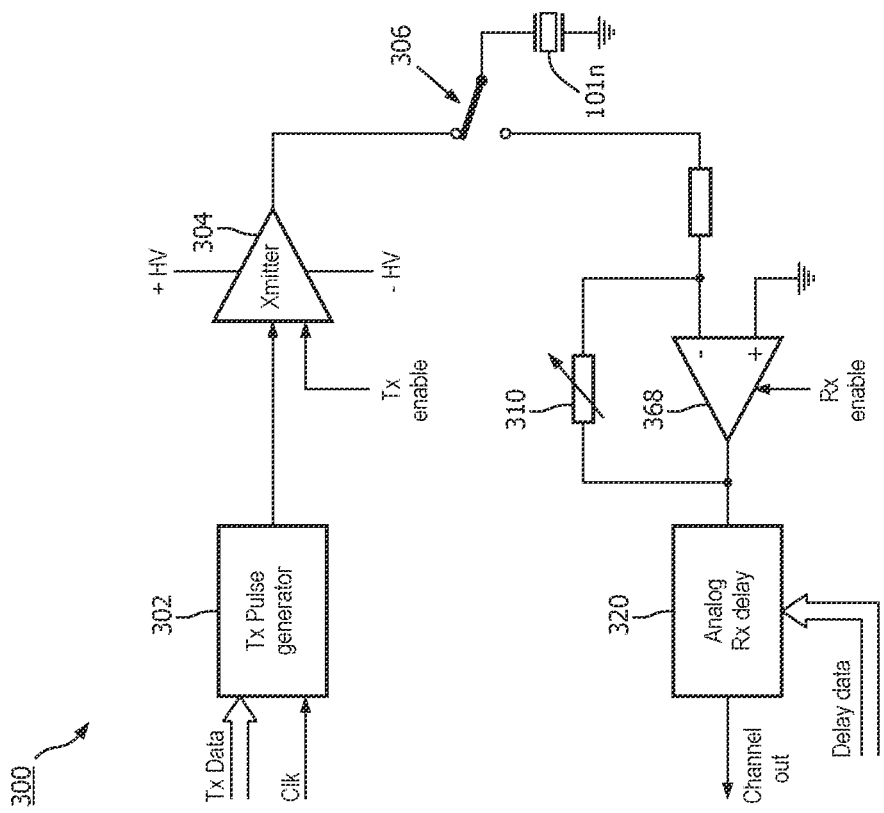
FIG. 3 illustrates in block diagram form the components of an analog ASIC of the microbeamformer of FIG. 2.

FIG. 3 illustrates the components of one channel 300 of the analog ASIC 102. In the illustrated implementation each analog ASIC has components for 4096 analog channels connected to 4096 elements of the matrix array 101. Transmit data (Tx Data) is received by a transmit pulse generator 302 from the FPGA 104. The FPGA has accessed this data from the RAM memory 110 for a desired transmit/receive sequence in response to a command previously received from the system controller 26, which itself is acting in response to an imaging selection entered by a user on user interface 20. The Tx Data controls parameters of a transmit pulse such as pulse width, transmit delay relative to a time marker, and pulse count. The Tx Data is clocked into the transmit pulse generator 302 which responds by developing the desired sequence of transmit pulse events. The transmit pulse sequence is applied to the input of a high voltage transmitter 304 at the time of a transmit enable signal (Tx Enable). The high voltage transmitter 304 drives an element 101n of the matrix array with a high voltage transmit waveform when transmit/receive (T/R) switch 306 is set to couple the transmitter to the transducer element as shown in the drawing. Following the transmission of the waveform into the subject, the T/R switch 306 is set to the alternate position so that the electrical signals transduced in response to received acoustic echoes are coupled to the input of a preamplifier 68 (also referred to as a preamlifying amplifier). A receive enable signal (Rx Enable) enables the preamplifier during the period of echo signal reception. The gain of the preamplifier 68 is increased during the period of echo reception, providing a TGC gain characteristic to signals received from increasing depths of the subject. The gain may be adjusted digitally by a controllable feedback impedance 310 which is implemented in integrated circuit form as a plurality of switchable parallel impedances. As more digitally controlled switches of the parallel impedances are closed, more impedances are coupled in parallel, reducing the feedback impedance 310 of the preamplifier. See, e.g., US patent application no. [2016PF00604], (Freeman et al.) The amplified analog echo signals are coupled to an analog receive delay circuit 320 which delays the received echo signals in relation to the delays applied to other echo signals by the channels of other elements of the patch for analog beamforming. The applied delay is controlled by Delay Data received from the FPGA 104. The delayed echo signals are applied to a summing node with the other analog signals of the patch, shown as Channel Out in the drawing, where the echo signals are summed in the form of patch sum analog signals. In the preferred implementation for a 2D array, there are 128 summing nodes producing the partial sum signals from 128 patches of sixty-four elements each. These 128 partial sum signals are the input signals for the digital ASICs 103 which perform multiline digital beamforming.

Figure 4:
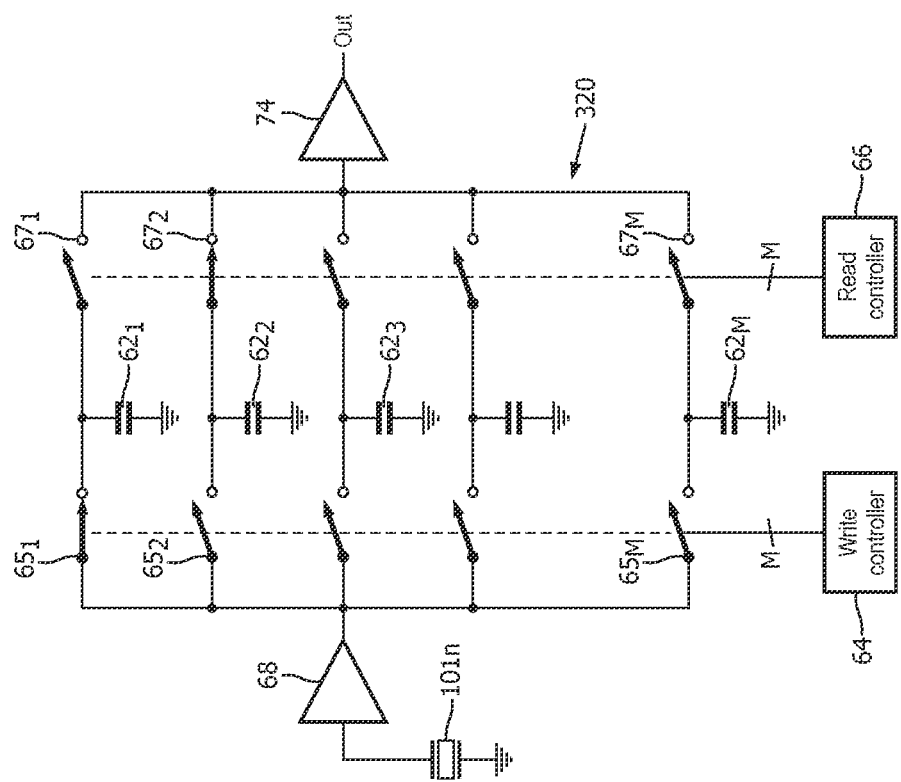
FIG. 4 is a circuit diagram of the analog receive delay of the analog ASIC of FIG. 3.

FIG. 4 illustrates an integrated circuit implementation of the analog receive delay circuit 320. The circuit 320 is a capacitive circuit which samples the signal produced by a transducer element 101n by closure of a switch 65, stores the sample on a capacitor 62 of the circuit, and then, at a later time which defines the intended delay, the sample is read from the capacitor by closure of a switch 62. The signal delayed in this manner is then coupled to the patch summing node by an output buffer 74, where it is summed with the analog signals from the other sixty-three elements of the patch. The time that a signal is stored on a capacitor 621, 622, . . . 62m is determined by the operation of a write controller 64 and a read controller 66. The write controller is a pointer circuit which determines the closure of one of switches 651, 652, . . . 65m, the brief closing of which samples the signal of transducer 101n at the output of preamplifier 68 and stores the sample on a capacitor. After a switch has "written" one sample to a capacitor, the write controller closes another switch 65 to store another sample of the signal on another capacitor 62. The write controller thus stores in rapid succession a plurality of samples of the signals received by transducer element 101n during the period of echo reception. The frequency with which samples are acquired exceeds the Nyquist rate for the received frequency band, and is usually well in excess of this rate. The read controller 66 is a pointer circuit which operates in a similar manner to read the stored signal samples after they have been stored on the capacitors for the desired delay period. The read controller closes one of switches 67, coupling a stored signal sample to an output buffer 74 from which it is available for further processing. In a rapid succession a sequence of the sampled signals are read from capacitors 62 and the now-delayed samples are forwarded for summation at the patch summing node.

The components of the analog ASIC 102 are seen to be digitally controlled analog components, and the transmitter 304 and T/R switch 306 must be capable of operating at the high voltages needed to drive a transducer element. In a preferred implementation the analog ASICs are manufactured by an integrated circuit process suitable for high voltages and with a relatively large feature size such as 0.18 μM.

Figure 5:
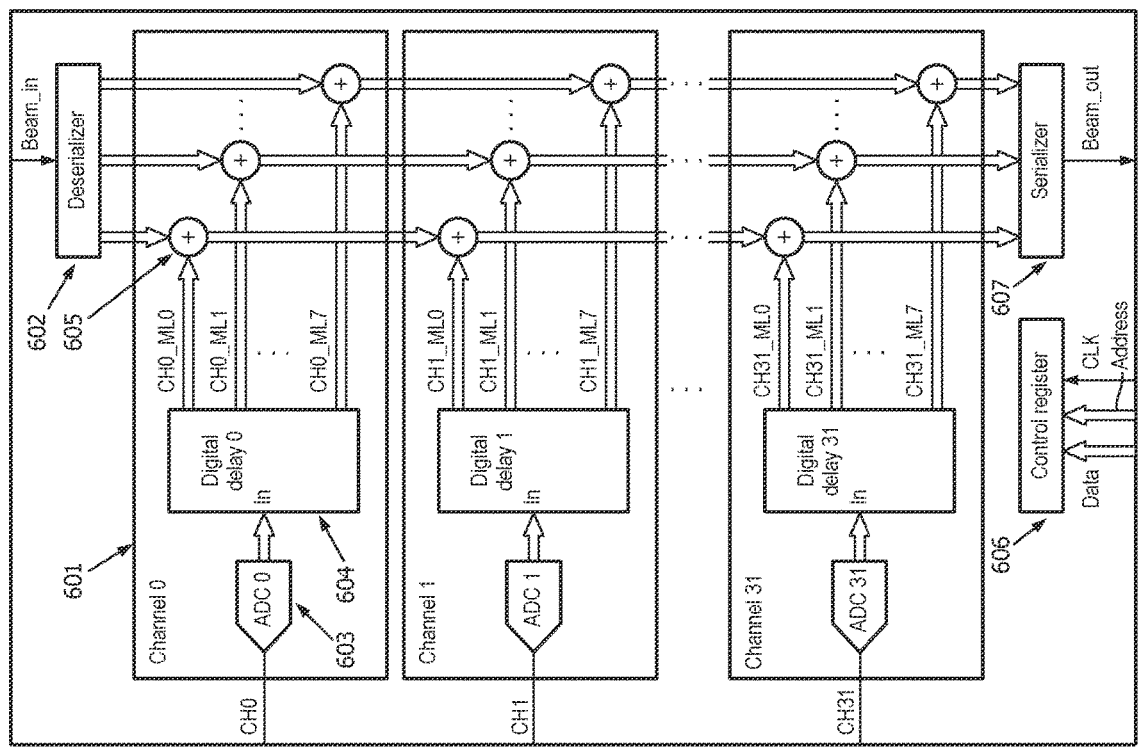
FIG. 5 illustrates in block diagram form the components of a digital ADC and beamforming ASIC of FIG. 3.

The circuitry of the four digital ASICs 103 is shown in FIG. 5. In the illustrated implementation each digital ASIC contains 32 digital channels 601 to process the summed analog signals from 32 patches of transducer elements. Each digital channel digitizes an analog patch signal and forms eight digital multiline output signals so that eight receive beams, each of a sequence of digital echo signals, are formed simultaneously. The eight multiline output signals are shown as ML0 to ML7 for each channel in the drawing. The degree of multiline may be 4×, 8× as shown in FIG. 5, 16× or any higher order multiline as determined by the circuit designer. In operation, an analog patch signal is converted to a sequence of digital echo samples by a low power ADC 603, preferably one which consumes 10 milliwatts or less, such as a successive approximation type ADC or a delta-sigma ADC. Each digital echo sample is delayed by eight selectable delay increments by a digital delay circuit 604, producing delayed echo signals for eight multilines. The eight multiline samples ML0-ML7 are coupled to eight digital adders or summers (summing circuits) 605, where the samples are summed with digital echo samples produced by other channels. The digital echo samples of the eight multilines from a preceding digital ASIC are received as a high rate serial data stream by a deserializer 602, which sorts samples of the data stream into eight parallel lines for the eight multilines. The thirty-two channels of the ASIC then add their partial sum multiline signals to the data of these eight parallel lines at a lower data rate than the high rate of the serial data stream. For instance, the serial data stream may run at 160 MHz, whereas other circuitry on the digital ASIC is clocked at 20 MHz. At the output of the ASIC (bottom right in the drawing), the data of the eight parallel lines is rearranged into a high rate serial data stream by a serializer 607, which is coupled to the next digital ASIC for summation with digital partial sum signals from other channels. Like the deserializer 602, the serializer 607 runs at the higher data rate. At the output of the last digital ASIC in the chain, the fully beamformed serial data (RECEIVE BEAM DATA) is coupled to the FPGA 104 which applies the received beam data to the USB controller 105 for communication to the image display device 108. Each digital ASIC also contains control registers 606 which receive control data from the FPGA to set parameters of the digital conversion and beam formation process, such as sampling times and delay values for the digital delay circuits 604.

In the digital ASIC shown in FIG. 5, the integrated circuit process used is preferably one with a smaller feature size than that of the analog ASIC, which must operate at high voltages. A suitable feature size for the digital ASIC is 65 nM or less, which allows higher circuit density than that of the analog ASIC while conserving power. Reduced power consumption is further facilitated by operating most of the digital ASIC at a lower clock rate than that for which the integrated circuit process is capable. As previously mentioned, the serializer and deserializer operate at a high frequency such as 160 MHz, so the chosen integrated circuit process must be capable of running at that clock frequency. But the digital ASIC core, in particular the digital delays and summers, is clocked at 20 MHz. This low frequency of operation, much lower than that for which the circuitry is designed, further reduces the power required by the digital ASICs 103, since power consumption is proportional to clock frequency. Moreover, the lower clock rate of data reduces the need for resynchronization registers between circuits, further reducing power consumption. Furthermore, by operating the digital ASIC at a lower clock frequency, lower supply voltages can be used than would otherwise be necessary to maintain the desired precision at a higher clock frequency. Since power consumption is a function of voltage, operation at a lower voltage also saves power. In a preferred implementation the ADCs and the serializers and deserializers of the digital ASICs are operated at a higher voltage and the ASIC core at a lower voltage.

Figure 5A:
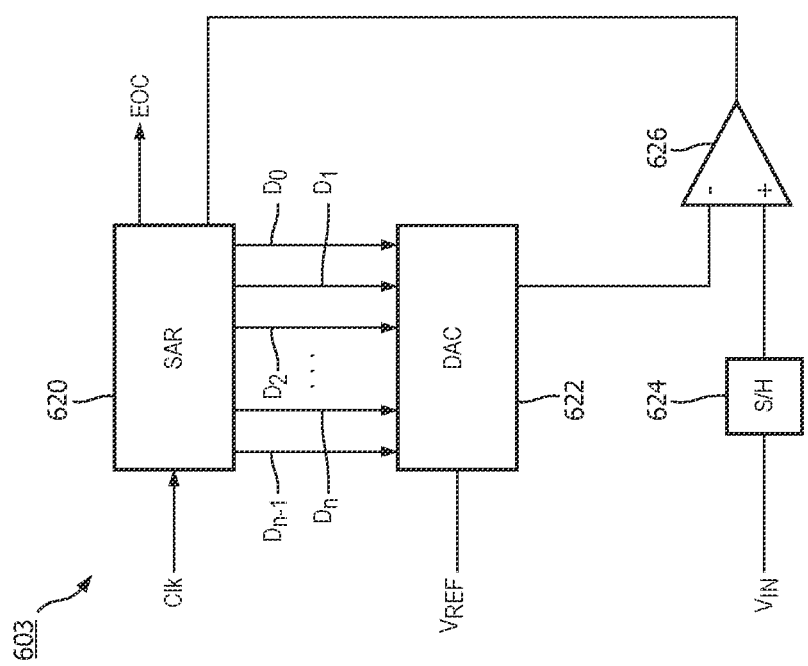
FIG. 5a illustrates in block diagram form a successive approximation analog-to-digital converter suitable for use in the digital ASIC of FIG. 5.

FIG. 5a illustrates the architecture of a low power successive approximation ADC 603. The analog echo signal to be converted, $V_{IN}$ in the drawing, is sampled and held by sample-and-hold circuit 624. A successive approximation register (SAR) 620 is initialized so that its most significant output bit $D_n$ is set to a value of one. A digital-to-analog converter (DAC) 622 produces a comparison voltage referenced to voltage $V_{REF}$ which is the analog equivalent of an n+1 bit digital word with its most significant bit ($D_n$) set to one. A comparator 626 compares the analog echo signal with the comparison voltage and if the comparison voltage is greater than the analog echo signal, the comparator output causes the SAR to set the most significant bit to zero; otherwise, it is left at a value of one. The next most significant bit of the SAR, $D_{n-1}$, is set to one, and another comparison is performed to determine the correct setting of the $D_{n-1}$ bit. The process is completed until all of the output bits of the SAR have been correctly set, which is then the digital value of the analog echo signal. An end-of-conversion signal EOC signals this completion of the conversion to the digital delay circuit 604, which then accepts the digital value of the SAR as its next digital signal sample. The sample-and-hold circuit 624 then acquires a new echo signal sample, the SAR 620 is initialized, and the process continues.

Figure 6:
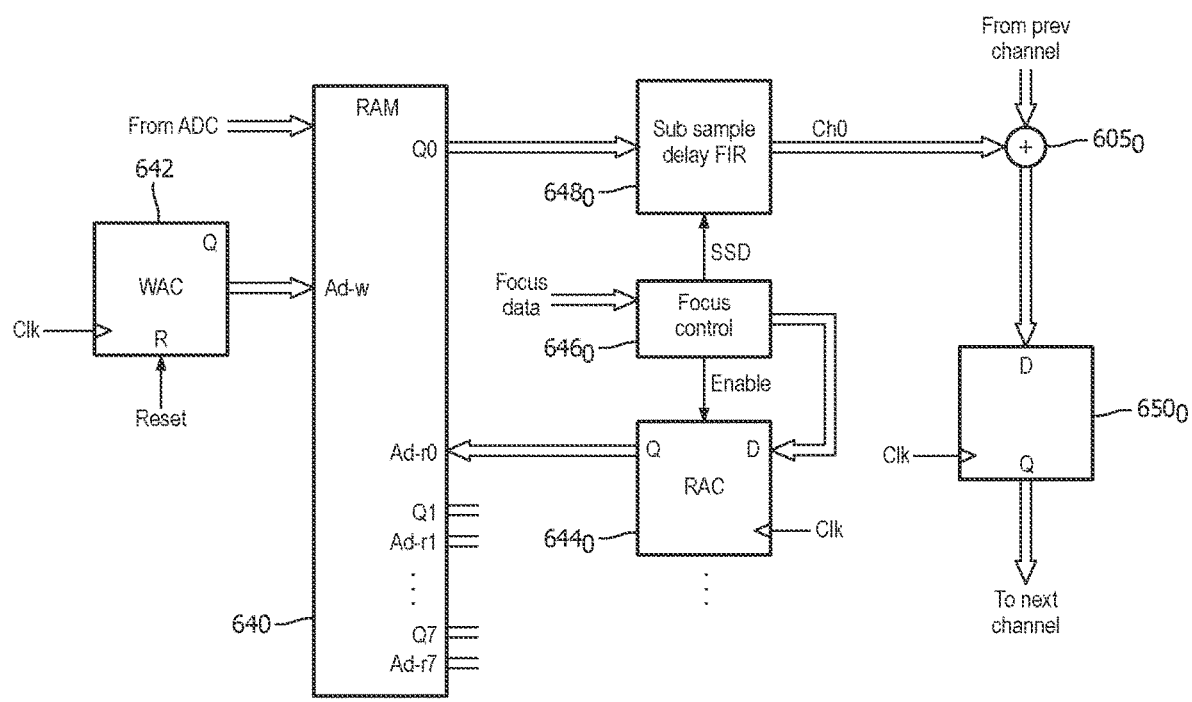
FIG. 6 illustrates the digital delay, delay control, and summation circuitry of one channel of the digital ASIC of FIG. 5.

The digital delay circuitry, delay control, and summation circuitry of one channel of the digital ASIC of FIG. 5 is shown in further detail in FIG. 6. As the low power ADC 603 produces successive digital echo signal samples from a patch, the samples are stored in a multi-port RAM 640 by the indexing of a write address counter (WAC) 642. Delayed echo signals are read out of eight output ports $Q_0$-$Q_7$ of the RAM 640 by eight read address counters (RAC) $644_0$ to $644_7$ for eight multilines, the circuitry of one of which is shown in the drawing. Additional read address counters can be added when more than eight multilines are to be produced. Each RAC 644 applies its read address to one of the eight address ports Ad-r0 to Ad-r7 of the RAM. The address of the read-out sample and its timing determine the delay of the digital echo signal. The addresses applied to the RAM for a multiline are set by a focus control circuit $646_0$ in response to focus data provided by the FPGA 104, and the output addresses are clocked into the RAC $644_0$ and periodically adjusted for dynamic focusing. The delayed digital echo signals produced at the Q outputs of the RAM 640 can be further resolved to a finer delay by a sub sample delay FIR $648_0$, which also receives data as required from the focus control circuit. The final delayed digital echo signal for a multiline, shown as CH0 in the drawing, is summed with other samples for that multiline from other digital channels by a summer $605_0$. The summed samples up to that point are resynchronized by clocking into a D type flip-flop $650_0$ and applied to the summer of the next channel. Each channel thus produces properly delayed digital patch signal samples for eight multilines ($Q_0$-$Q_7$) simultaneously.

Figure 7:
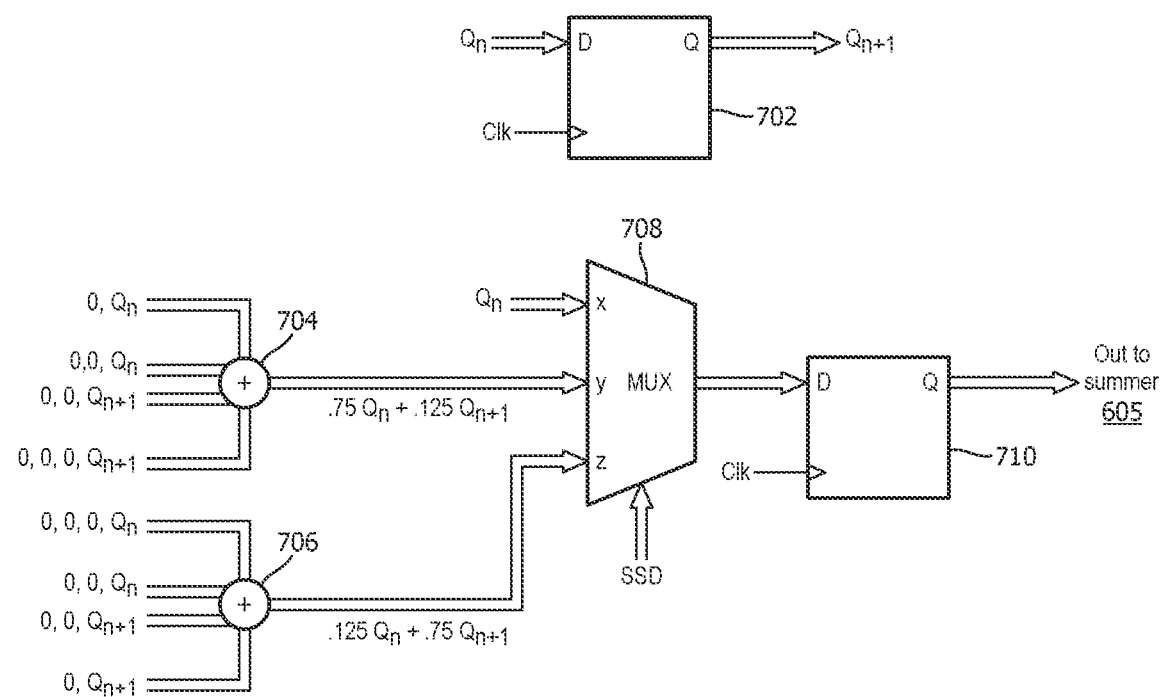
FIG. 7 illustrates the digital FIR (finite impulse response) filter used for sub sample delay in the digital ASIC of FIG. 5.
Figure 8:
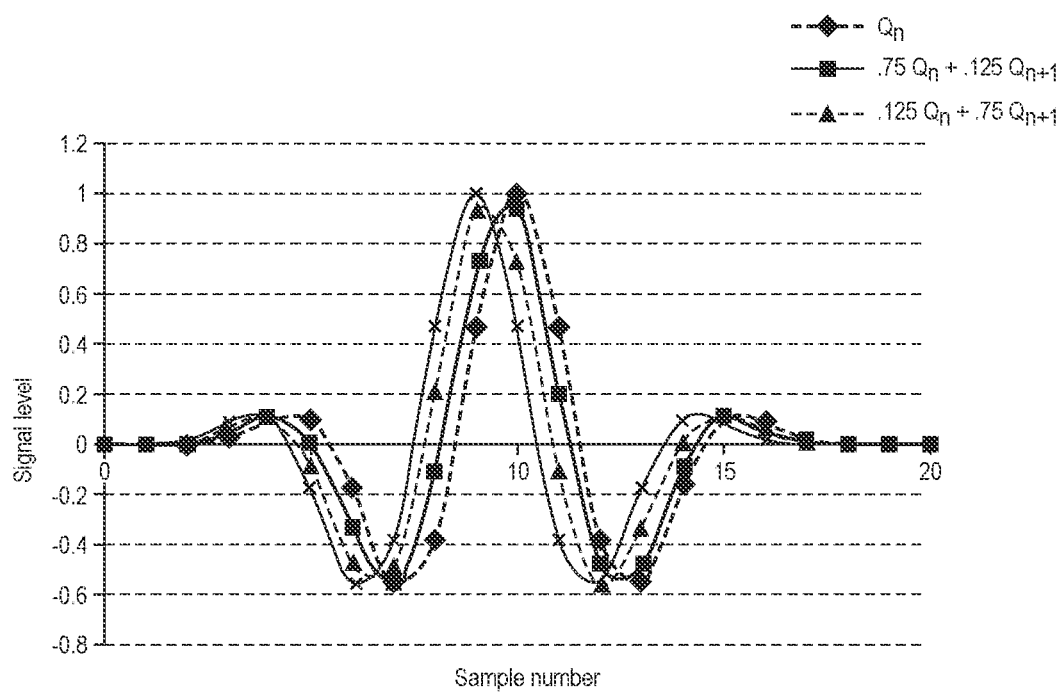
FIG. 8 illustrates echo signal waveforms with different delays as produced by the sub sample delay FIR of FIG. 7.

A preferred sub sample delay finite impulse response (FIR) filter is shown in FIG. 7. This preferred FIR filter, unlike conventional FIR filters, uses no multipliers, thereby conserving power. Successive echo signal samples from the RAM 640 are clocked into a register 702, which thus has a current sample $Q_n$ at its input and the previous sample $Q_{n+1}$ at its output. Weighted fractions of the two samples are formed to produce more finely resolved delayed sample values. Instead of using multipliers to do the weighting, the weighting fractions used are to a power of two, formed by forced zero-filling of one or more of the most significant bits of a sample value. Thus, a summer 704 is coupled to receive the $Q_n$ sample weighted twice, once with its most significant bit zeroed $(0,Q_n)$ and again with its two most significant bits zeroed $(0,0,Q_n)$. Similarly, the summer 704 is also coupled to receive the $Q_{n+1}$ sample in two weighted forms, once with the two most significant bits zeroed and again with the three most significant bits zeroed. The summer 704 thus produces a weighted echo signal of the form $0.75Q_n+0.125Q_{n+1}$. In like manner a summer 706 is coupled to produce a weighted echo signal of the form $0.125Q_{n+1}0.75Q_{n+1}$. The $Q_n$ sample and these two weighted sample values are applied to the three inputs of a multiplexer 708 and one of the applied values is selected as the multiplexer output value by an SSD selection signal provided by the focus control circuit 646. The selected finely delayed value is clocked into a register 710 for resynchronization and applied to a summer 605 for that multiline. FIG. 8 shows three phase shifts of a typical ultrasound echo signal which can be produced by the sub sample delay FIR filter of FIG. 7. As seen, delay values of 0, ⅓ and ⅔ of a base sampling clock frequency can be achieved with this circuitry.

An important feature of the digital ASIC of FIG. 5 for reduced power consumption is that the ADCs 603 and the following digital beamforming (digital delays 604 and summers 605) are located in the same integrated circuit package. This eliminates the need to transfer data from an ADC in one package to the digital beamformer in another package, which would require increased power in order to drive signals from one package to another through the intervening IC pins, PCB traces, and connection pads. Power is saved by this use of in-package interconnection. While the digital ASIC package can employ stacked dies or a multi-chip module, it is preferred that the ADC be on the same silicon die as the digital beamformer circuitry.

It should be noted that the various embodiments described above and illustrated by the exemplary ultrasound systems of FIGS. 1 and 2 may be implemented in hardware, software or a combination thereof. The various embodiments and/or components of an ultrasound system, for example, the modules, or components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system. The computer or processor may also include a memory. The memory devices described above may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including a microbeamformer may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine. In the ultrasound system of FIG. 2, for instance, software instructions are received by the FPGA 104 of the microbeamformer from the mainframe ultrasound system. The FPGA then applies the software instructions to the analog and digital ASICs 102 and 103 to control the operation of the microbeamformer structural components by software instructions.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasound probe for digital microbeamforming, comprising: a two-dimensional array transducer; a digital microbeamformer comprising: a plurality of transmitters coupled to the array; a plurality of amplifiers coupled to the a rray a nd configured to receive analog echo signals from transducer elements of the array during a receive period; a plurality of low-power delta-sigma or successive approximation analog-to-digital converters (ADCs) coupled to the amplifiers and configured to receive amplified analog echo signals and convert them to digital echo data; a microbeamformer controller; a power supply; and a digital output circuit configured to provide the digital echo data to a system beamformer, the system beamformer disposed in an ultrasound system external to the ultrasound probe, wherein the digital microbeamformer is configured to consume three watts or less during operation.

2. The ultrasound probe of claim 1, wherein the digital echo data comprises partially-beamformed echo signals.

3. The ultrasound probe of claim 1, wherein the transducer comprises transducer elements comprising a piezoceramic material.

4. The ultrasound probe of claim 1, wherein the transducer comprises capacitive micro-machined ultrasonic transducer (CMUT) elements.

5. The ultrasound probe of claim 1, wherein the low power ADCs are adapted to perform analog to digital conversion by successive approximation.

6. The ultrasound probe of claim 1, wherein the low power sigma-delta or successive approximation ADCs and the digital beamforming circuitry are located in a first integrated circuit package.

7. The ultrasound probe of claim 6, wherein the transmitters and the amplifiers are located in a second integrated circuit package.

8. The ultrasound probe of claim 7, wherein the two dimensional array transducer comprises a matrix array transducer bonded to the second integrated circuit package.

9. The ultrasound probe of claim 8, wherein the two-dimensional array transducer is flip chip bonded to the second integrated circuit package.

10. The ultrasound probe of claim 1, wherein the low power ADCs comprise delta-sigma analog-to-digital converters.

11. The ultrasound probe of claim 1, wherein the plurality of transmitters and the plurality of amplifiers are located in two sepa rate integrated circuit packages, each containing both transmitters and amplifiers.

12. The ultrasound probe of claim 11, wherein the plurality of low power ADCs and the digital beamforming circuitry comprise a 128 channel digital beamformer.

13. The ultrasound probe of claim 1, wherein the digital beamforming circuitry comprises a plurality of digital delay circuits and a plurality of digital summers.

14. The ultrasound probe of claim 1, wherein the microbea mformer controller comprises a control FPGA.

15. The ultrasound probe of claim 1, wherein the power supply comprises a switched power supply.

16. The ultrasound probe of claim 1, wherein the digital output circuit comprises a USB controller.

17. An ultrasound system, comprising: an ultrasound probe for digital microbeamforming, the probe comprising a two-dimensional a rray tra nsducer, a digital microbeamformer, the digital microbeamformer having a plurality of transmitters coupled to the array, a plurality of amplifiers coupled to the array and configured to receive analog echo signals from transducer elements of the array during a receive period, a plurality of low-power delta-sigma or successive approximation analog-to-digital converters (ADCs) coupled to the amplifiers and configured to receive amplified analog echo signals and convert them to digital pa rtially-bea mformed echo signals, a microbeamformer controller, a power supply, and a digital output circuit configured to provide the digital partially-beamformed echo signals to a system beamformer that is disposed in an ultrasound system, wherein the digital microbeamformer is configured to consume three watts or less during operation; an ultrasound system mainframe comprising the system beamformer; and a cable configured to transmit the partially-beamformed echo signals from the digital output circuit to the system beamformer.

18. The ultrasound system of claim 17, wherein the cable is one of a Universal Serial Bus (USB) cable, an Ethernet cable, and an HDMI cable.

19. The ultrasound system of claim 17, wherein the digital output circuit is configured to transmit the pa rtially-bea mformed echo signals as serial data.

* * * * *